| United States Patent [19] | [11] 3,985,768 |
| --- | --- |
| Priestap et al. | [45] Oct. 12, 1976 |

[54] PROCESS FOR PRODUCING ROLITETRACYCLINE

[75] Inventors: Horacio Alfredo Priestap, Martinez; Carlos Rappaport, Olivos, both of Argentina

[73] Assignee: E. R. Squibb & Sons, Inc., Princeton, N.J.

[22] Filed: Jan. 23, 1975

[21] Appl. No.: 543,576

[30] Foreign Application Priority Data

Feb. 20, 1974 Argentina .......................... 252437

[52] U.S. Cl. ........................ 260/326.33; 260/326.85; 260/559 AT; 424/274
[51] Int. Cl.² ........................................ C07D 207/06

[58] Field of Search ............................. 260/326.33

[56] References Cited

UNITED STATES PATENTS 3,104,240   9/1963   Cheney et al. .................. 260/247.2

*Primary Examiner*—Nicholas S. Rizzo
*Assistant Examiner*—Mary C. Vaughn
*Attorney, Agent, or Firm*—Lawrence S. Levinson; Merle J. Smith

[57] ABSTRACT

Rolitetracycline is prepared by a process which comprises reacting tetracycline with methylene-bis-pyrrolidine and formaldehyde or paraformaldehyde.

8 Claims, No Drawings

PROCESS FOR PRODUCING ROLITETRACYCLINE

SUMMARY OF THE INVENTION

This invention relates to an improved method of producing rolitetracycline.

Rolitetracycline [N-(1-pyrrolidinylmethyl)tetracycline] is a broad spectrum antibiotic which is generally prepared by a Mannich reaction from tetracycline, formaldehyde or polymer thereof and pyrrolidine (U.S. Pat. No. 3,104,240). It has been found, however, that an improved process results that gives better yields, reduces water formation during synthesis, avoids the caustic action of pyrrolidine on tetracycline and by-passes an intermediate which discolors easily and transmits color to the final product, when the reaction is effected using methylene-bis-pyrrolidine [J. Org. Chem. 19, 1862 (1954); 29, 402 (1964); 30, 2787 (1965)].

According to this invention N,N'-methylene-bis-pyrrolidine is produced by heating formaldehyde or paraformaldehyde in an inert organic solvent, preferably a lower alkanol like ethanol, with pyrrolidine. The preformed methylene-bis-pyrrolidine is added to tetracycline base and formaldehyde or paraformaldehyde to complete the reaction.

The formation of the methylene-bis-pyrrolidine is preferably carried out under reflux conditions. The solvent can be separated and the product purified by distillation.

The reaction of the methylene-bis-pyrrolidine is preferably carried out using tetracycline base in an inert organic solvent such as methylene chloride or a lower alkanol like methanol or ethanol and at about ambient temperature, e.g., about 20° to 25° C. According to the preferred modification, the tetracycline, methylene-bis-pyrrolidine and formaldehyde compound are used in mole proportions of about 2:1:1, respectively, although these may deviate to the extent of about 50%. It is preferable, though not necessary, to seed the reaction mixture, crystallization of the desired product being facilitated thereby. If the materials used are sterile and the processing is carried out under sterile conditions, a sterile product is produced. It is also preferable to use anhydrous conditions throughout.

The following example is illustrative of the invention. All temperatures are on the centigrade scale.

EXAMPLE 4.42 kg. of paraformaldehyde are suspended in 10 liters of anhydrous ethanol in a distillation flask with reflux. The suspension is heated under reflux at atmospheric pressure. 24.6 liters of redistilled pyrrolidine are added slowly. Heating is continued until dissolution is completed. The ethanol is then removed by distillation under vacuum at 40°. The N,N¹-methylene-bis-pyrrolidine is purified by distillation at 68°–73° and 5 to 6 mm. Hg.

450 liters of methylene chloride are added to a dry stainless steel tank and the temperature is adjusted within the range 20° to 25°. 45 kg. of tetracycline base are added with agitation. When dissolution is complete, the material is passed through a pressure filter and then a sterilizing filter into a sterile crystallizer. A solution of formaldehyde in ethanol, providing 0.047 kg. of formaldehyde per kg. of tetracycline (ca. 42% w/v; ca. 5 liters) is passed through a sterilizing filter then into the crystallizer under agitation. This is stirred for 15 minutes. 7.26 kg. of methylene-bis-pyrrolidine is passed through a sterilizing filter and collected in sterile bottles. 3.63 kg. of the methylene-bis-pyrrolidine is added to the crystallizer. The reaction mixture is seeded with 50 g. of sterile rolitetracycline and stirred for one hour. The remaining 3.63 kg. of methylene-bis-pyrrolidine is added and agitation is continued for 2 additional hours. The crystal slurry is drained, placed in a horizontal pressure filter and the mother liquor is removed under nitrogen pressure. The product is washed with 3 × 80 l. of methylene chloride. The rolitetracycline crystals are dried in a shelf drier under steam ejector vacuum at 60° for 10 hours then under high vacuum at 60° for another 20 hours. The dried product is then ground in a hammer mill, passed through a 2A mesh sieve and then stored in refrigerated stainless steel containers under nitrogen.

What is claimed is:

1. A process for the production of rolitetracycline which comprises reacting preformed methylene-bis-pyrrolidine with tetracycline and formaldehyde or paraformaldehyde at about ambient temperature in an inert organic solvent.

2. A process as in claim 1 wherein the solvent is methylene chloride.

3. A process for the production of rolitetracycline which comprises adding preformed methylene-bis-pyrrolidine to tetracycline and formaldehyde in an inert organic solvent at about 20° to 25° C and removing rolitetracycline from the reaction mixture.

4. A process as in claim 3 wherein the solvent is methylene chloride.

5. A process as in claim 4 wherein the process is effeced under sterile conditions.

6. A process for the production of rolitetracycline which comprises reacting formaldehyde or paraformaldehyde with pyrrolidine by heating in an inert organic solvent at a temperature up to about reflux temperature, separating methylene-bis-pyrrolidine therefrom, adding said methylene-bis-pyrrolidine to a mixture of tetracycline base and formaldehyde in an inert organic solvent, and separating rolitetracycline.

7. A process as in claim 6 wherein the solvent is ethanol.

8. A process as in claim 6 wherein the solvent is methylene chloride.

* * * * *